United States Patent
Hong et al.

(10) Patent No.: US 8,034,634 B2
(45) Date of Patent: *Oct. 11, 2011

(54) ULTRA-SENSITIVE MAGNETOREDUCTION MEASUREMENT SYSTEM AND ULTRA-SENSITIVE, WASH-FREE ASSAY USING THE SAME

(76) Inventors: Rex Chih-Yih Hong, Taipei (TW);
Herng-Er Horng, Taipei (TW);
Hong-Chang Yang, Taipei (TW);
Shieh-Yueh Yang, Sindian (TW)

( * ) Notice: Subject to any disclaimer, the term of this patent is extended or adjusted under 35 U.S.C. 154(b) by 734 days.

This patent is subject to a terminal disclaimer.

(21) Appl. No.: 11/867,207

(22) Filed: Oct. 4, 2007

(65) Prior Publication Data

US 2008/0024117 A1    Jan. 31, 2008

Related U.S. Application Data

(63) Continuation-in-part of application No. 11/563,035, filed on Nov. 24, 2006, now Pat. No. 7,394,246, and a continuation-in-part of application No. 11/422,336, filed on Jun. 6, 2006, now abandoned, which is a continuation-in-part of application No. 11/164,275, filed on Nov. 16, 2005, now Pat. No. 7,560,289.

(51) Int. Cl.
*G01N 33/533* (2006.01)
*G01N 33/543* (2006.01)

(52) U.S. Cl. ........................................ 436/526; 436/518

(58) Field of Classification Search .................. 436/526, 436/518
See application file for complete search history.

(56) References Cited

U.S. PATENT DOCUMENTS

| | | | | |
|---|---|---|---|---|
| 3,826,972 A * | 7/1974 | Day et al. | .................. | 324/313 |
| 5,256,541 A * | 10/1993 | Pouletty et al. | .............. | 435/7.24 |
| 5,268,305 A * | 12/1993 | Ribi et al. | ...................... | 436/501 |
| 6,825,655 B2 * | 11/2004 | Minchole et al. | ............. | 324/204 |
| 7,514,207 B2 * | 4/2009 | Jacks et al. | ......................... | 435/4 |
| 7,560,289 B2 * | 7/2009 | Hong et al. | .................. | 436/526 |
| 2003/0092029 A1 * | 5/2003 | Josephson et al. | ................. | 435/6 |

FOREIGN PATENT DOCUMENTS

| | | |
|---|---|---|
| JP | 63-90765 | 4/1988 |
| JP | 2001-510565 | 7/2001 |
| JP | 2005-527782 | 9/2005 |

OTHER PUBLICATIONS

Chinese First Examination Report of China Application No. 200810083022.3, dated on Jan. 10, 2011.
"Office Action of Japan Counterpart Application", issued on Jun. 1, 2011, p1-p3, in which the listed references were cited.

* cited by examiner

*Primary Examiner* — Jacob Cheu
*Assistant Examiner* — Pensee Do
(74) *Attorney, Agent, or Firm* — J.C. Patents

(57) ABSTRACT

An ultra-sensitive, wash-free method for quantitatively determining the concentration of biomolecules in a sample solution is provided. The sensitivity of the method is 1 ppt or below. The method includes providing a reagent containing magnetic nanoparticles and measuring the ac magnetic susceptibility of the reagent. Then, a sample solution containing either multiple-active epitope biomolecules or single-active-epitope biomolecules is mixed with the reagent. The ac magnetic susceptibility of the reagent after the association with the biomolecules is measured. Thereafter, the difference in the ac magnetic susceptibility of the reagent before and after the association with the biomolecules is measured and the concentration of biomolecules in the sample solution is determined.

12 Claims, 9 Drawing Sheets

(a)

ULTRA-SENSITIVE MAGNETOREDUCTION MEASUREMENT SYSTEM AND ULTRA-SENSITIVE, WASH-FREE ASSAY USING THE SAME

CROSS-REFERENCE TO RELATED APPLICATION

This application Ser. No. 11/867,207, PG Pub. No. 20080024117, filed Oct. 4, 2007 is a continuation-in-part of prior application Ser. No. 11/563,035, filed on Nov. 24, 2006, now U.S. Pat. No. 7,394,246, and of prior application Ser. No. 11/422,336, filed on Jun. 6, 2006, now abandoned, which is a continuation-in-part of prior application Ser. No. 11/164,275, filed on Nov. 16, 2005, now U.S. Pat. No. 7,560,289. The entirety of each of the above-mentioned patent applications is hereby incorporated by reference herein and made a part of this specification.

BACKGROUND OF THE INVENTION

1. Field of Invention

The present invention relates to a system for measuring a concentration of biomolecules and a method of measuring a concentration of biomolecules using the same. More particularly, the present invention relates to an ultra-sensitive magnetoreduction measurement system and an ultra-sensitive, wash-free assay using the same.

2. Description of Related Art

To measure the concentration of biomolecules in a specimen, such as serum or urine, immunoassay, which is based on the reaction of an antibody or antibodies to its antigen, is often applied. One such immunoassay is the enzyme-linked immunosorbent assay (ELISA). The conventional ELISA (or the so-called sandwich ELISA) requires one antibody (captured antibody) being bound to a solid phase attached to the bottom of a plate well. The sample with the unknown amount of antigen is then added and allowed to complex with the bound antibody. After the antigen is immobilized, another antibody (detection antibody) with the same antigen specificity as the immobilized captured antibody is added to form a complex with the antigen. The detection antibody can then be covalently linked to an enzyme. Between each step, the plate is typically washed to remove any unbound proteins or antibodies. After the final wash step, the plate is developed by adding a chromogenic substrate or fluorogenic substrate to produce a signal that indicates the quantity of biomolecules in the sample. In essence, the sandwich ELISA requires two kinds of antibodies (captured antibodies and detection antibodies). Further, the two kinds of antibodies bind to epitopes that do not overlap on the antigen. Basically sandwich ELISA is inapplicable for detecting molecules having a single active epitope, for example, small molecules. Other methodologies, such as competitive ELISA, LC/MS/MS (Liquid Chromatography/Mass Spectrometry/Mass Spectrometry), high-performance liquid chromatograph, capillary electrophoresis, have also been applied to assay single-active-epitope biomolecules. However, these methods are normally non-direct, costly or involve complicated sample preparation or assay processes.

In recent years, alternative approaches have been explored to quantitatively detect biomolecules. For example, bio-functionalized magnetic nanoparticles, in which the surfaces of magnetic nanoparticles are coated with bio-receptors, have been used to mark specific biomolecules. Then, the differences in the magnetic properties of the biomolecules marked by or conjugated with the bio-functionalized magnetic nanoparticles are measured for determining the amounts of the biomolecules. These assays using bio-functionalized magnetic nanoparticles as markers are referred to as magnetically labeled diagnosis (MLD).

Several groups of researchers have reported high potential methodologies for MLD, for example, the measurements of magnetic relaxation, magnetic remenance, mixed-frequency magnetic susceptibility, saturated magnetization, etc. According to the results from these methodologies of MLD, some have demonstrated the merit of high convenience, while others exhibit the advantage of high sensitivity.

SUMMARY OF THE INVENTION

The present invention provides an ultra-sensitive, magnetoreduction measurement system for assaying biomolecules, wherein the sensitivity of the ultra-sensitive magnetoreduction measurement system is 1 ppt (parts per trillion) or below.

The present invention also provides an ultra-sensitive magnetoreduction measurement system which is capable of measuring the amounts of multiple-active-eptiope biomolecules or single-active-eptiope biomolecules, wherein the single-active-eptiope biomolecules includes small biomolecules.

As embodied and broadly described herein, the ultra-sensitive magnetoreduction measurement system of the invention includes a sample unit and a sensor unit, wherein a sample containing magnetic nanoparticles is housed in the sample unit and the magnetization of the sample is transferred to a magnetometer in the sensor unit via a couple coil.

In accordance with the ultra-sensitive magnetoreduction measurement system of the invention, the magnetometer is spatially far from the sample and the excitation magnetic fields provided to the sample. Hence, the magnetometer remains undisturbed and the sensitivity of the measurement is enhanced.

In accordance with the ultra-sensitive magnetoreduction measurement system of the invention, wherein the magnetometer includes a superconducting quantum interference device (SQUID).

In accordance with the ultra-sensitive magnetoreduction measurement system of the invention, wherein the magnetometer is a high-transition-temperature (high-$T_c$) rf (radio frequency) SQUID.

In accordance with the ultra-sensitive magnetoreduction measurement system of the invention, the sample unit further includes two excitation coils to supply a magnetic flux to the sample.

In accordance with the ultra-sensitive magnetoreduction measurement system of the invention, the sample unit further includes a pick-up coil, wherein the sample that includes at least bio-receptor-coated magnetic nanoparticles is configured inside one section of the pick-up coil.

In accordance with the ultra-sensitive magnetoreduction measurement system of the invention, the pick-up coil is connected with the couple coil.

In accordance with the ultra-sensitive magnetoreduction measurement system of the invention, wherein the system measures the ac magnetic susceptibility of the sample, wherein the difference in the ac magnetic susceptibility of the sample before and after the biomolecules are associated with the magnetic nanoparticles increases with the increasing amount of the biomolecules.

The present invention provides an ultra-sensitive method for quantitatively determining the amount of biotargets, wherein the sensitivity of the method is about 1 ppt or below.

The present invention also provides an ultra-sensitive method for quantitatively determining the amount of biotargets, wherein a high level of specificity is achieved.

The present invention provides an ultra-sensitive method for quantitatively determining the amount of biotargets, wherein the method is capable of quantitatively measuring the amount of multiple-active-eptiope biomolecules or single-active-eptiope biomolecules, wherein, the single-active-eptiope biomolecules further includes small molecules.

The present invention provides an ultra-sensitive method for quantitatively determining the amount of biotargets, wherein the method is substantially free of wash processes between steps.

As embodied and broadly described herein, the ultra-sensitive method of the invention includes providing a magnetic reagent, measuring the ac magnetic susceptibility of the magnetic reagent ($\chi_{ac,o}$), mixing the magnetic reagent with the sample solution containing the biotargets, measuring the ac magnetic susceptibility of the magnetic reagent after mixing with the sample solution ($\chi_{ac,\phi}$), and calculating a difference in the ac magnetic susceptibility of the reagent before and after the mixing with the biomolecules ($\Delta\chi_{ac,\phi}$), wherein $\Delta\chi_{ac,\phi} \equiv (\chi_{ac,o} - \chi_{ac,\phi})$.

According to the method of the invention, a characteristic curve between the $\Delta\chi_{ac,\phi}$ and various known concentrations of the biotargets is established and the concentration of the biotargets in the sample solution is determined according to the characteristic curve.

According to the method of the invention, a normalized characteristic curve between the $\Delta\chi_{ac,\phi}/\chi_{ac,o}$ and various known concentrations of the biotargets is established and the concentrations of the biotargets in the sample solution is determined according to the characteristic curve.

According to the method of the invention, wherein a parameter $\Delta\chi_{ac,\phi}/\chi_{ac,o}$ is defined as an indicator for a concentration of the biotargets, where $\Delta\chi_{ac,\phi}/\chi_{ac,o} = (\chi_{ac,o} - \chi_{ac,\phi})/\chi_{ac,o}$.

According to the method of the invention, the magnetic reagent is formed by suspending magnetic nanoparticles in a buffer solution with bio-receptors bound to the magnetic nanoparticles.

According to the method of the invention, the bio-receptors are capable of conjugating with the biotargets after the magnetic reagent is mixed with the sample solution.

According to the method of the invention, the magnetic nanoparticles are coated with a hydrophilic surfactant and the bio-receptors are bound to hydrophilic surfactant.

According to the method of the invention, the method is capable of measuring small biomolecules, in which when the small molecules are conjugated with the bio-receptors, each of the conjugated small molecule is substantially enveloped by one of the bio-receptors.

According to the method of the invention, the bio-receptors are antibodies.

According to the method of the invention, the antibodies can be monoclonal or polyclonal.

According to the method of the invention, the ac magnetic susceptibility is measured by a SQUID-based magnetoreduction measurement system.

According to the method of the invention, the magnetic reagent before and after mixing with the sample solution is placed inside one section of a pick-up coil in the sample unit of the SQUID-based magnetoreduction measurement system, and an induced magnetic flux from the magnetic reagent is detected by the pick-up coil and is transferred to the SQUID magnetometer in the sensor unit of the SQUID-based magnetoreduction measurement system via the couple coil connected with the pick-up coil in the sample unit.

According to the method of the invention, the step of measuring the ac magnetic susceptibility of the magnetic reagent after mixing with the sample solution ($\chi_{ac,\phi}$) is performed without having to remove the free, un-conjugated magnetic nanoparticles or biotargets.

According to the method of the invention, the hydrophilic surfactant includes but not limited to dextran, protein G, protein A, liposome, and organic acids.

According to the method of the invention, wherein a diameter of each magnetic nanoparticle ranges from 5 nm to 700 nm.

According to the method of the invention, the core material of the magnetic nanoparticles includes but not limited to $Fe_3O_4$, $MnFe_2O_4$, $Fe_2O_3$, $NiFe_2O_4$ or $CoFe_2O_4$.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

The present invention provides an alternative methodology for the magnetically labeled diagnosis (MLD), in which the amount of the to-be-measured biotargets can be correlated with the degree of reduction in multiple-frequency ac magnetic susceptibility of the magnetic nanoparticles after the magnetic nanoparticles are conjugated with the biotargets. The method of the invention is thus known as magnetoreduction assay (MRA), which is basically free from wash processes between steps and is capable of assaying on multiple-active-epitope molecules, single-active-epitope molecules or small molecules. The present invention also provides an ultra-sensitive system to perform the magnetoreduction assay. The ultra-sensitive MRA system of the invention adopts magnetometers or gradiometers, such as a superconducting quantum interference device (SQUID) as sensors for the system and applies the flux-transfer technology in order to perform assays with high sensitivity, which is particularly requisite for certain kinds of bio-targets, such as cytokines or vascular endothelial growth factor (VEGF) or a protein expressed by tumors.

Magnetoreduction Assay (MRA)

In MRA, a magnetic reagent, which is a solution having homogeneously dispersed magnetic nanoparticles coated with a hydrophilic surfactants and bio-receptors, is first provided. The preparation of the reagent principally includes mixing magnetic nanoparticles in a surfactant solution for coating the surfaces of the magnetic nanoparticles with the surfactant. The bio-receptors are then added to the solution and to bind with the surfactants on the surface of the magnetic nanoparticles. The bio-receptors include, for example, antibodies or antigens, which can be monoclonal or polyclonal. Under external multiple ac magnetic fields, the magnetic nanoparticles oscillate via magnetic interaction. The magnetic reagent under the external multiple ac magnetic fields manifests a magnetic property, known as multiple-frequency ac magnetic susceptibility $\chi_{ac}$.

Figure 1:
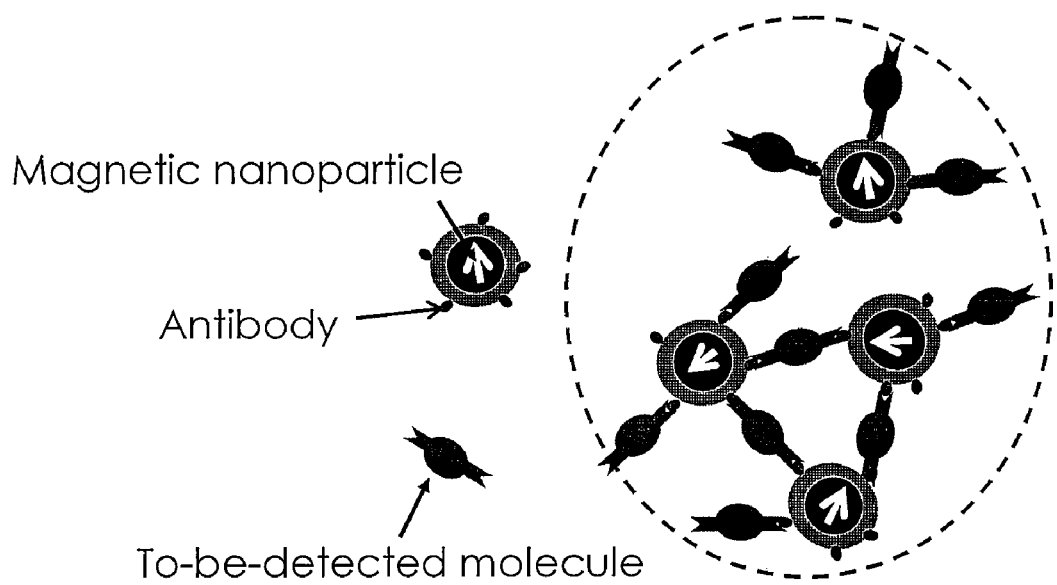
FIG. 1 is a schematic diagram showing the association between the to-be-detected bio-molecules and magnetic nanoparticles coated with antibody, and the magnetic nanoparticles become clustered due to the binding with to-be-detected bio-molecules, as circled with the dashed line.
Figure 2:
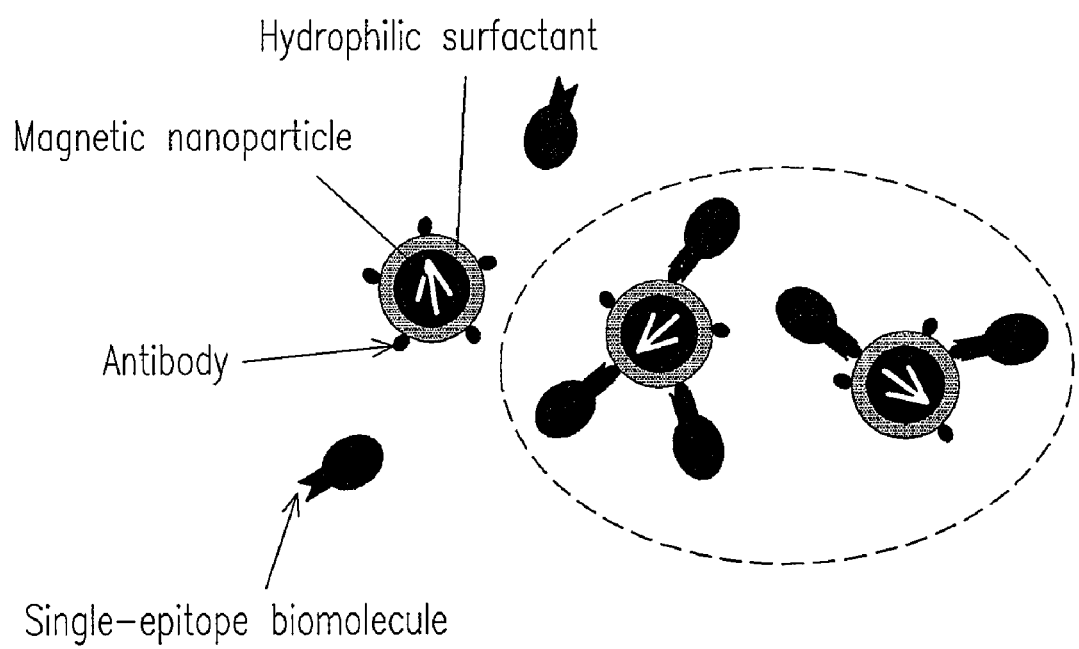
FIG. 2 is a schematic diagram showing the association between the to-be-detected bio-molecules and magnetic nanoparticles coated antibody, and the magnetic nanoparticles become larger due to the binding with to-be-detected bio-molecules, as circled with the dashed line.

When a solution of the to-be-detected biomolecues is mixed with the reagent, the to-be-detected biomolecules may become associated with the surfactant-and-bio-receptor-coated magnetic nanoparticles through the bio-receptors bound to the outmost shell of the magnetic nanoparticles. Due to the association with the to-be-detected biomolecules, the surfactant-and-bio-receptor-coated magnetic nanoparticles either become larger or form clusters as shown in the schematic illustration in FIG. 1. In the situation that the biomolecules have only one effective single active eptiope, each biomolecule only conjugates with or binds to one magnetic nanoparticle. Hence, the magnetic nanoparticles would become larger instead of forming clusters as shown in FIG. 2.

After being associated with the biomolecules, the response of these larger/clustered magnetic nanoparticles to the external multiple ac magnetic fields would become much lower than that of the originally un-conjugated, individual magnetic nanoparticles. Hence, the $\chi_{ac}$ of the reagent is reduced. Accordingly, this method is referred as a magnetoreduction assay. In principle, when more amounts of the to-be-detected biomolecules are mixed into the reagent, more magnetic nanoparticles become larger or clustered. Ultimately, a larger reduction in $\chi_{ac}$ is observed.

The MRA of the present invention presents at least the following merits. First of all, it is unnecessary to remove the unbounded to-be-detected biomolecules and magnetic nanoparticles. These unbounded biomolecules and magnetic nanoparticles may remain in the regent. Hence, the assay process of the invention is simpler by obviating the tedious washing processes. Secondly, only one kind of antibody is used. Thirdly, MRA is direct and homogeneous assay, which usually shows high reliability and sensitivity. Fourthly, because the degree of reduction in $\chi_{ac}$ can be accurately measured to correspond to the concentration of the biomolecules, the concentration of the biomolecules can be quantitatively determined. Additionally, MRA is capable of measuring small biomolecules. Due to the small size, the small molecules are almost fully enveloped by the bio-receptor after the association. Accordingly, once a small molecule is conjugated with a bio-receptor, other epitope on the small molecule is unavailable to be bound to other bio-receptors. Hence, small biomolecules are effectively single-active-epitope due to their structure.

In brief, the MRA of the present invention has been demonstrated for not only its convenience since the series of wash processes can be eliminated, it is highly sensitive and has a high level of specificity.

SQUID-Based MRA System

Since the ac magnetic signals of samples are detected in MRA, the sensitivity in detecting biomolecules can be promoted by either using an ultra-sensitive sensor to probe the ac magnetic signals or by enhancing the ac magnetic signals to be detected. It has been demonstrated that the superconducting quantum interference devices (SQUIDs) are promising candidates as sensors in an MRA system.

In magnetoreduction measurements, the difference in the ac magnetic susceptibility $\chi_{ac}$ of a magnetic reagent before and after the bio-targets have been added therein and conjugated with the bio-receptors on the magnetic nanoparticles is measured under the actions of two excitation magnetic fields. The SQUID is disturbed by the two excitation magnetic fields when a magnetic reagent is positioned closed to the SQUID. As a result, it is necessary to have coils generating fields to compensate for the contribution from the excitations fields to the SQUID. Technically, it is not easy to identify the right position for the compensations coils, and the noise level usually increases with the use of the compensation coils, which serve as pick-up coils for the SQUID to sense ambient noises. Instead of using compensation coils, another way to prevent the SQUID from being disturbed by the excitation fields is by positioning the samples together with the excitation fields far away from the SQUID sensor. However, such an approach would lead to a significant decrease in the magnetic signals detected by the SQUID, which in turns, diminishes the sensitivity. To overcome such deficiency, a SQUID-based MRA system has been developed by utilizing the distant flux transfer technology.

Figure 3:
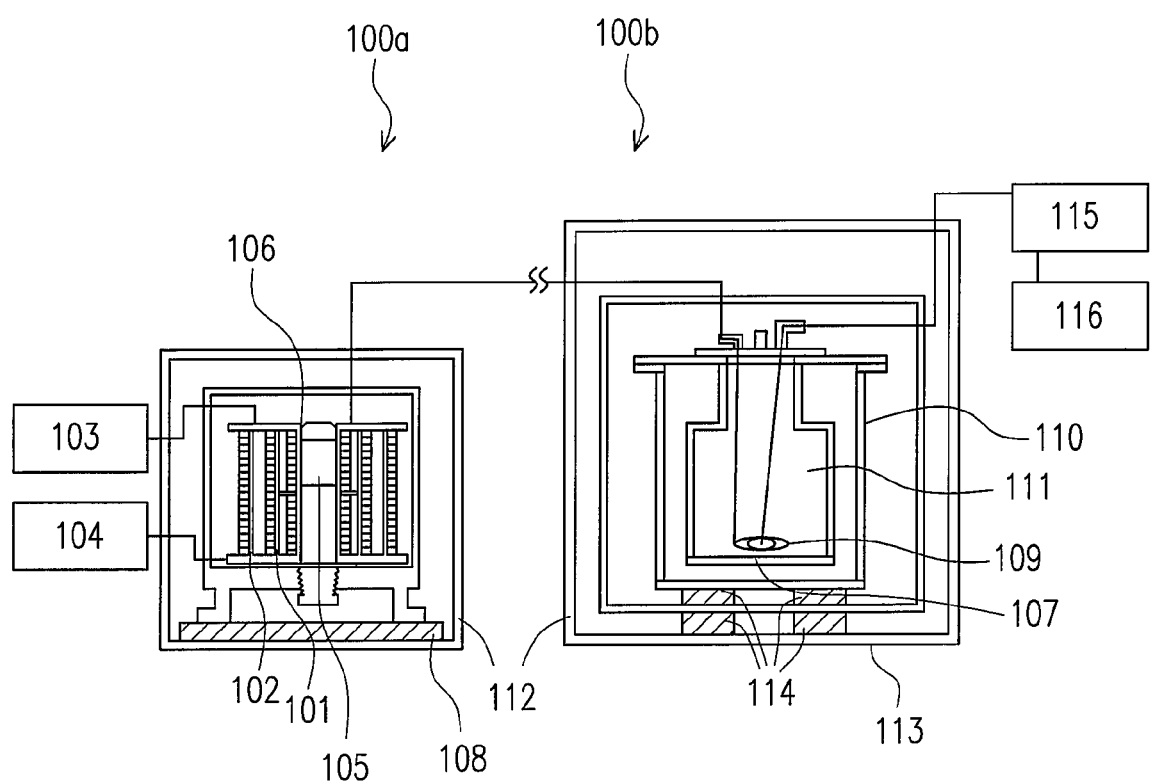
FIG. 3 is a schematic diagram illustrating the SQUID-based MRA system assisted with flux-transfer technology.

Referring to FIG. 3, FIG. 3 is a schematic diagram illustrating the SQUID-based MRA system according to the present invention. In general, the system comprises two units: the sample unit 100a and the sensor unit 100b. The sample unit 100a includes at least two excitation coils 101, 102 driven by two independent function generators 103, 104 to provide a to-be-detected sample 105 with two ac excitation magnetic fields having frequencies $f_1$ and $f_2$, respectively. The sample 105 is placed inside one section of a pick-up coil 106, which is constructed of two sections of coils wired in opposite directions. The ac magnetization of the sample 105 under the actions of the two excitation magnetic fields is detected by the pick-up coil 106. To avoid mechanical vibration and ambient noises, the coils of the sample unit 100a are placed on a sponge 108 and inside a magnetically shielded box 112. The sensor unit 100b includes at least a high-transition-temperature (high-$T_c$) rf SQUID magnetometer 109, which is immersed in liquid nitrogen contained a dewar 110. It should be appreciated that other types of SQUID magnetometers or gradiometers may also be used as sensors in the system of the present invention, even including low-transition-temperature SQUIDs immersed in liquid helium contained in a dewar. The dewar 110, capable of holding 5 L of liquid nitrogen 111 for example, is configured inside the magnetically shielded box and a rf shielded room 113 to prevent the SQUID from the environmental low- or high-frequency noises. The shielded factor approaches 90 dB at high frequencies. A sponge 114 is used to insulate the SQUID from mechanical vibrations.

To transfer the ac magnetization of a sample sensed by the pick-up coil at the sample part to the SQUID at the sensor part, a couple coil 107 manufactured from copper (Cu) and connected with the pick-up coil is used. Due to the ac magnetic flux through the pick-up coil 106, voltage is induced, and then a current is generated along the pick-up coil 106 and the couple coil 107. When the ac current flowed through the couple coil, an ac magnetic field is generated. The SQUID is positioned inside the couple coil, so that the ac magnetic field generated by the couple coil is probed by the SQUID. According to the SQUID-based MRA system of the invention, the ac magnetic flux originally generated at the sample part is efficiently transferred to the sensor part of the SQUID-based MRA system via a transfer set consisted of a pick-up coil 106 and a couple coil 107. With this setup, the SQUID is undisturbed by the two excitation fields because the excitation fields are spatially far from the SQUID. Thus, the system is very stable and is suitable for long-time operation. The SQUID electronics 115 and read-out electronics 116 are used for the SQUID to detect the ac magnetic flux originally generated by the sample at the sample part. The output voltages from the electronics are fed into a spectrum analyzer. Then, the ac magnetic susceptibility signal is analyzed at a certain frequency ($mf_1+nf_2$) using the spectrum analyzer, where m and n are non-zero and positive integers.

Magnetoreduction Measurement Using SQUID-Based MRA System

The following disclosures are examples of the application of the high-$T_c$ SQUID-based MRA system with flux transfer of the present invention on the assaying of the various types of bio-targets. In accordance with one aspect of the invention, exemplary assaying specifications of the SQUID-based MRA system of the present invention on "large" bio-targets, such as human c-reactive protein (CRP, molecular weight=116.67 KDa) and human coagulation factor IX (F9, molecular weight=36.56 KDa) are discussed. To magnetically label CRP, polyclonal anti-goat-CRP is coated onto the magnetic nanoparticles, while monoclonal anti-mouse-F9 is coated onto magnetic nanoparticles to magnetically label F9. Hence, the to-be-detected CRP functions as a multiple-active-epitope, while F9 functions as a single-active-epitope molecule. In accordance to another aspect of the invention, exemplary assaying specifications of the SQUID-based MRA system of the present invention on "small" bio-targets, for example, leucomalachite green (LMG, molecular weight=26.3 Da) are also discussed. Due to the small size, small molecules are almost completely enveloped by antibody after association. Thus, once each small molecule is conjugated with an antibody, no other epitope on the small molecule is available to bind to other antibodies. Hence the small molecules are effectively single-active-epitope molecules due to their structure. To better illustrate the features of the ultra-sensitive immunoassay via the wash-free magnetic reduction measurements of the invention on multiple-active-epitope molecules, single-active-epitope molecules, and small molecules using the high-$T_c$ SQUID-based MRA system of the invention, the MRA results are compared with data obtained from ELISA.

I. Preparation of Bio-Receptors-Coated Magnetic Nanoparticles

Figure 4:
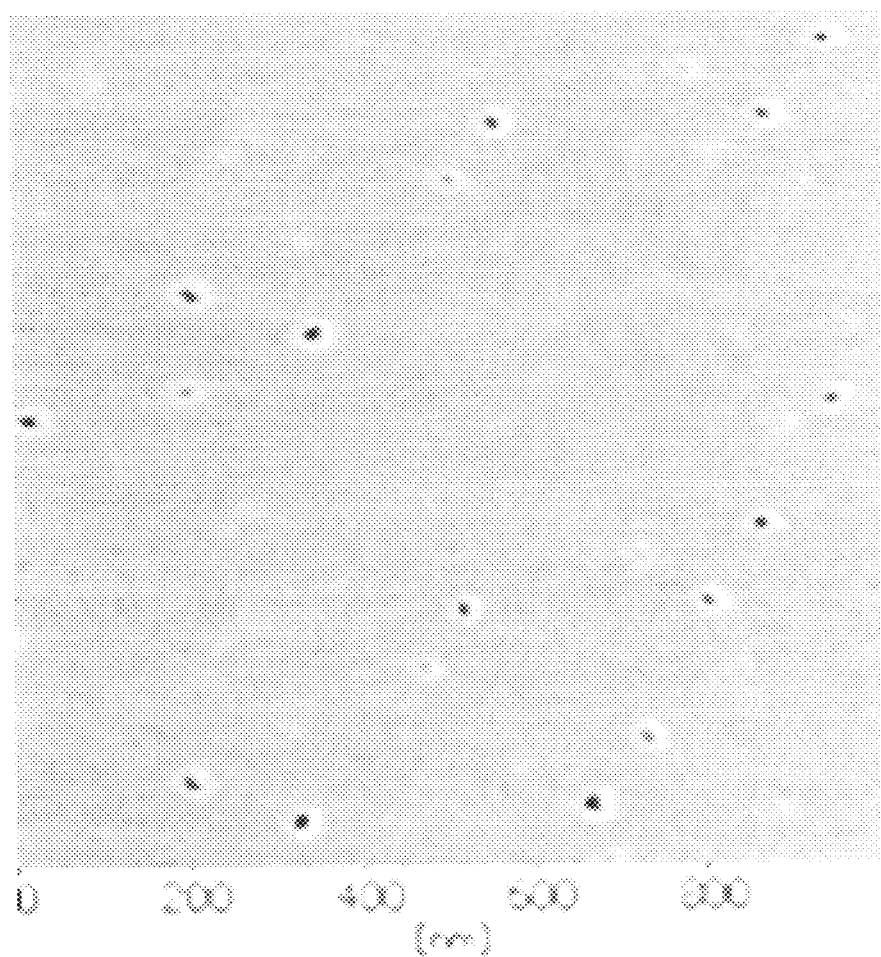
FIG. 4(a) is an image of dextran coated magnetic nanoparticles taken with a magnetic force microscope.
FIG. 4(b) is a curve showing the diameter distribution of dextran coated magnetic nanoparticles.
Figure 4:
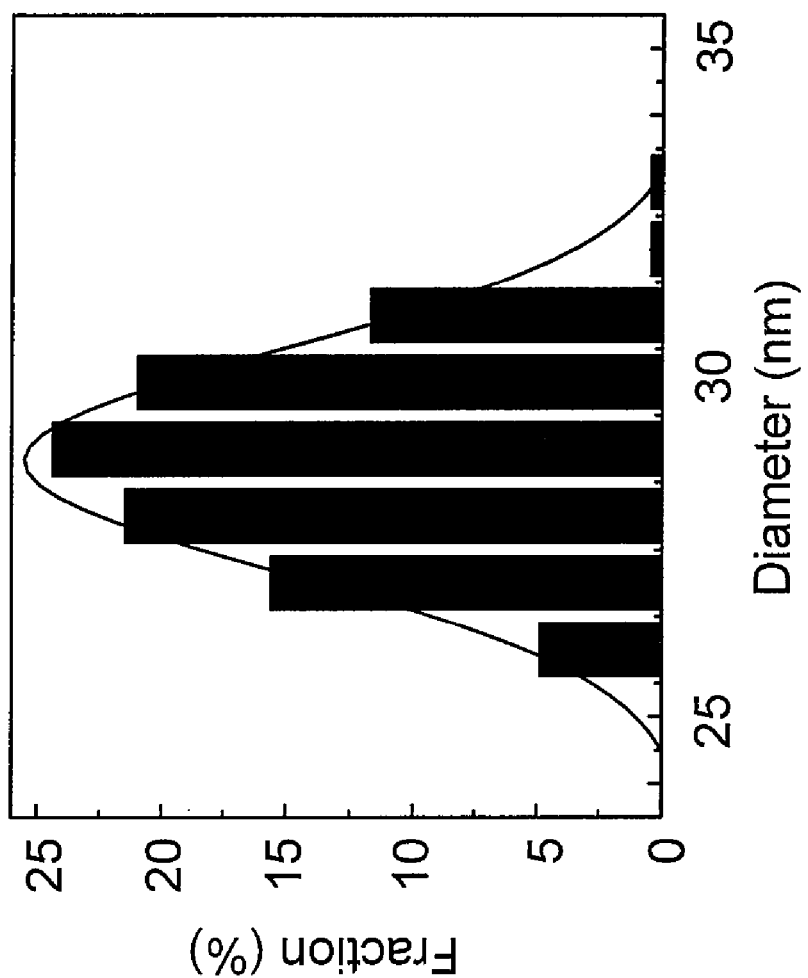

The magnetic nanoparticles dispersed in a phosphate buffer saline (PBS) solution are coated with a hydrophilic surfactant, such as dextran (GABC Co.). Other kinds of hydrophilic surfactant, for example protein G, protein A, liposome or organic acids, may also be applicable. The surfactant helps the dispersion of the magnetic nanoparticles in the PBS solution or alternatively improves the binding of the bio-receptors to the surface of the nanoparticles. The material of the core of the magnetic nanoparticles includes, for example, $Fe_3O_4$. However, it should be mentioned that other materials including $MnFe_2O_4$, $Fe_2O_3$, $NiFe_2O_4$ or $CoFe_2O_4$ are also applicable as the material of the magnetic nanoparticles and be comprised within the scope of the invention. By using a magnetic force microscope (MFM), the topology of magnetic nanoparticles is investigated. A typical image of magnetic nanoparticles taken by MFM is shown in FIG. 4(a). The dark spots correspond to the individual magnetic nanoparticles. Via the analysis of a large amount of magnetic nanoparticles, for example, more than two hundreds, the distribution of the diameter of magnetic nanoparticles is obtained, as plotted in FIG. 4(b). The guiding line in FIG. 4(b) follows Gaussian distribution. According to the results in FIG. 4(b), the mean value and the standard deviation in diameter of the magnetic nanoparticles are 29.3 nm and 1.4 nm, respectively. The mean diameter of magnetic nanoparticles used in following assays range from about 5 nm to about 700 nm.

To prepare a magnetic reagent, which is a solution of magnetic nanoparticles conjugated with bio-receptors to form the so-called bio-fanctionalized nanoparticles, a hydrophilic surfactant, for example, dextran, is first oxidized to create aldehyde groups (—CHO) on the surfactant. The bio-receptors, for example, antibodies such as polyclonal anti-goat-CRP (Sigma, C8284) or monoclonal anti-mouse-F9 (Abnova) are bound to the magnetic nanoparticles via a reaction between the bio-receptor and the aldehyde groups of the surfactant forming a "—CH=N—" bond. Through magnetic separation, the unbound bio-receptors are removed and the magnetic nanoparticles conjugated with bioreceptors are obtained. To magnetically label CRP, polyclonal anti-goat-CRP, for example, is used as the bio-receptor through the reactive process discussed above. To magnetically label F9, monoclonal anti-mouse-F9, for example, is used as the bio-receptor through the same reactive process discussed above. To magnetically label LMG, anti-rabbit-LMG (GlycoNex Inc.) is coated onto the nanoparticles through the surfactant on the surfaces of the nanoparticles and envelops substantially the entirety of the individual nanoparticle.

MRA Measurement

The ac magnetic susceptibility $\chi_{ac}$ spectra of 100-μl of the various magnetic reagents (the solutions of the polyclonal anti-goat-CRP-coated magnetic nanoparticles, the solution of the monoclonal anti-mouse-F9-coated magnetic nanoparticles, the solution of the anti-rabbit-LMG-coated magnetic nanoparticles, respectively) are measured using the SQUID-based MRA system. Then, each magnetic reagent is mixed with 20-μl solutions of various amounts of human CRP (Sigma, C4063) or F9 (Abnova) or LMG (GlycoNex Inc.), respectively, to form mixture solutions. Varying concentrations of immune complexes of CRP-anti-goat-CRP (or F9-anti-mouse-F9 or LMG-anti-rabbit-LMG) are developed in the mixture solutions after incubation. Thereafter, the $\chi_{ac}$ spectra of each mixture solution having immune complexes are analyzed by using the SQUID-based MRA system. A reduction in the $\chi_{ac}$ at a given frequency is observed for each reagent solution mixed with the various concentrations of CRP (or F9, or LMG). Hence, a relationship between a reduction in $\chi_{ac}$ and the concentration of CRP (or F9 or LMG) is established.

ELISA Measurement

A commercial assay kits (Anogen, EL 10022) of sandwich ELISA is used for quantitative detection of large molecules, such as human CRP. The assay procedure is described briefly herein. A 100-µl of human CRP is added to an ELISA plate, on the bottom of which an antibody pre-coated plate is seated. The well is covered with a plastic cover, and the CRP-antibody immune complex is incubated for 30 minutes. The solution is removed by filling the well with a wash buffer, and pouring the solution from the well. The wash process is repeated for four more times. After the final wash, the plate is inverted and is furthered dried by tapping the plate on an absorbent paper until no obvious moisture remained. Thereafter, 100-µl of HRP (horseradish peroxide)-conjugated marking solution is dispensed into the well, and the antibody-CRP-marker immune complex is then incubated for 30 minutes. A 100-µl fluorogenic substrate solution is then added to the well to activate the fluorescence for 15 minutes, followed by adding 100-µl stop solution to the well. Finally, the optical density of the fluorescence is measured with an ELISA reader (Synergy HT).

Sandwich ELISA is also used for assaying F9. A combination of anti-Human coagulation factor IX, F9 (Abnova, H00002158-M01) and polyclonal rabbit anti-GST antibody is used for quantitative detection of recombinant GST-tagged human F9 (H000002158-Q01). Human F9 antibody is initially coated on the microtiter plate at 1 µg/100 µl/well at 4° C. overnight. The wells are then blocked with 5% skim milk in PBS at room temperature for one hour. Different concentrations of recombinant GST-tagged human F9 in 100 µl of diluents were then added to appropriate wells. The plate is then incubated at room temperature for one hour. Goat anti rabbit InG (H+L), HRP secondary antibody is applied to the wells and the plate is incubated at room temperature for one hour. A 100-µl OPD substrate solution is then added to the well to develop for 30 minutes, followed by adding a stop solution into the well. Finally, the optical density of the solution in the wells is measured with an ELISA reader (BIO-TEK, uQuant).

Regarding small molecules such as LMG, sandwich ELISA is inapplicable. Instead, competitive ELISA (GlycoNex Inc., 101G002A) is used to quantitatively detect LMG. The general protocols for competitive ELISA are usually available in the manual of the assay kit and thus will not be further reiterated.

SQUID-Based MRA Measurement vs. ELISA

The results on CRP measured by the SQUID-based MRA system with ultra-high sensitivity vs. the conventional ELISA are summarized as follows. CRP is expressed when a human body is injured or infected. Hence, the CRP concentration in serum is a typical indicator for diagnosing infectious disease in clinics. The detailed mechanism of magnetic detection based on alternating current (ac) magnetic susceptibility reduction is discussed in the priority U.S. patent application Ser. No. 11/164,275, which is incorporated herein by reference.

Figure 5:
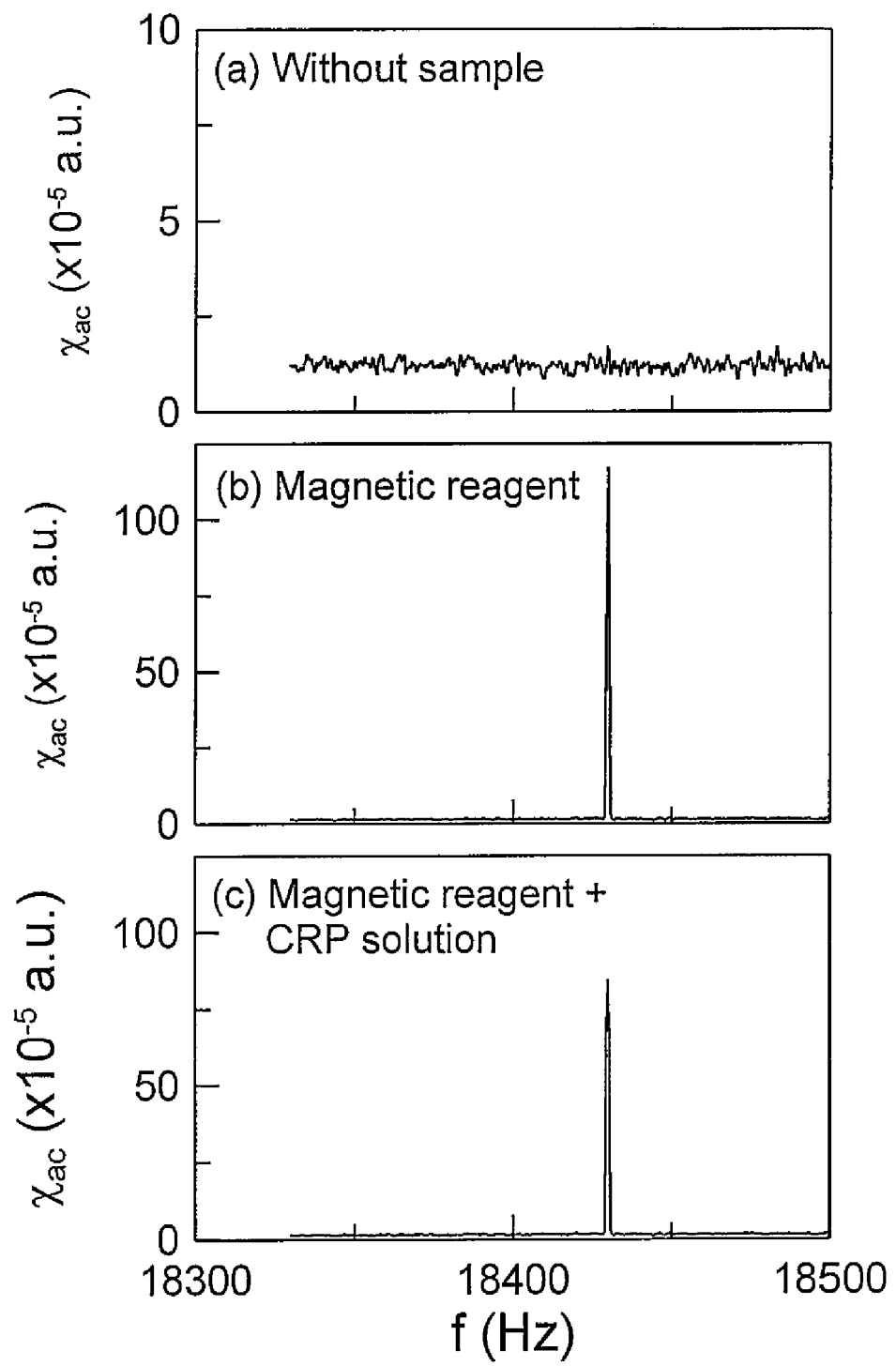
FIG. 5(a) is an $\chi_{ac}$ spectrum for the noise level of the SQUID-based MRA system.
FIG. 5(b) is an $\chi_{ac}$ spectrum for 100-μL and 0.32-emu/g magnetic reagent.
FIG. 5(c) is an $\chi_{ac}$ spectrum for a mixture of 100-μL and 0.32-emu/g magnetic reagent and 20-μL and $10^{-5}$-mg/L CRP solution.

The noise spectrum of the SQUID-based MRA around the target frequency $mf_1+nf_2$ is measured and is illustrated in FIG. 5(a), where $f_1$ and $f_2$ are excitation frequencies of several to tens of kHz, and m and n are non-zero integers. The results reveal a noise level at $1.7 \times 10^{-5}$ (a.u.) for the $\chi_{ac}$ spectrum. The frequency dependent $\chi_{ac}$ of the magnetic reagent is shown in FIG. 5(b) when the 100-µl magnetic reagent of 0.32 emu/g in concentration is located inside one section of the pick-up coil. A clear peak having a maximum value of $117 \times 10^{-5}$ (a.u.) is observed at $mf_1+nf_2$. This maximum value is referred to as $\chi_{ac,o}$. The results shown in FIG. 5(b) suggest a value of about 76 for the signal-to-noise ratio. The stable $\chi_{ac}$ spectrum is shown in FIG. 5(c) after adding 20-µl CRP solution of a given concentration $\phi_{CRP}$, for example, $10^{-5}$ mg/L, into the magnetic reagent. The maximum value of the peak at $mf_1+mf_2$ is $84.4 \times 10^{-5}$ (a.u.), which is referred to as $\chi_{ac,\phi}$. Apparently, $\chi_{ac,\phi}$ is smaller than $\chi_{ac,o}$. A parameter $\Delta\chi_{ac,\phi}/\chi_{ac,o}$ is defined as an indicator for the concentration of the amount of CRP, where $\Delta\chi_{ac,\phi}/\chi_{ac,o} \equiv (\chi_{ac,o}-\chi_{ac,\phi})/\chi_{ac,o}$. For $10^{-5}$ mg/L of CRP solution, $\Delta\chi_{ac,\phi}/\chi_{ac,o}$ is determined to be 27.9%.

Figure 6:
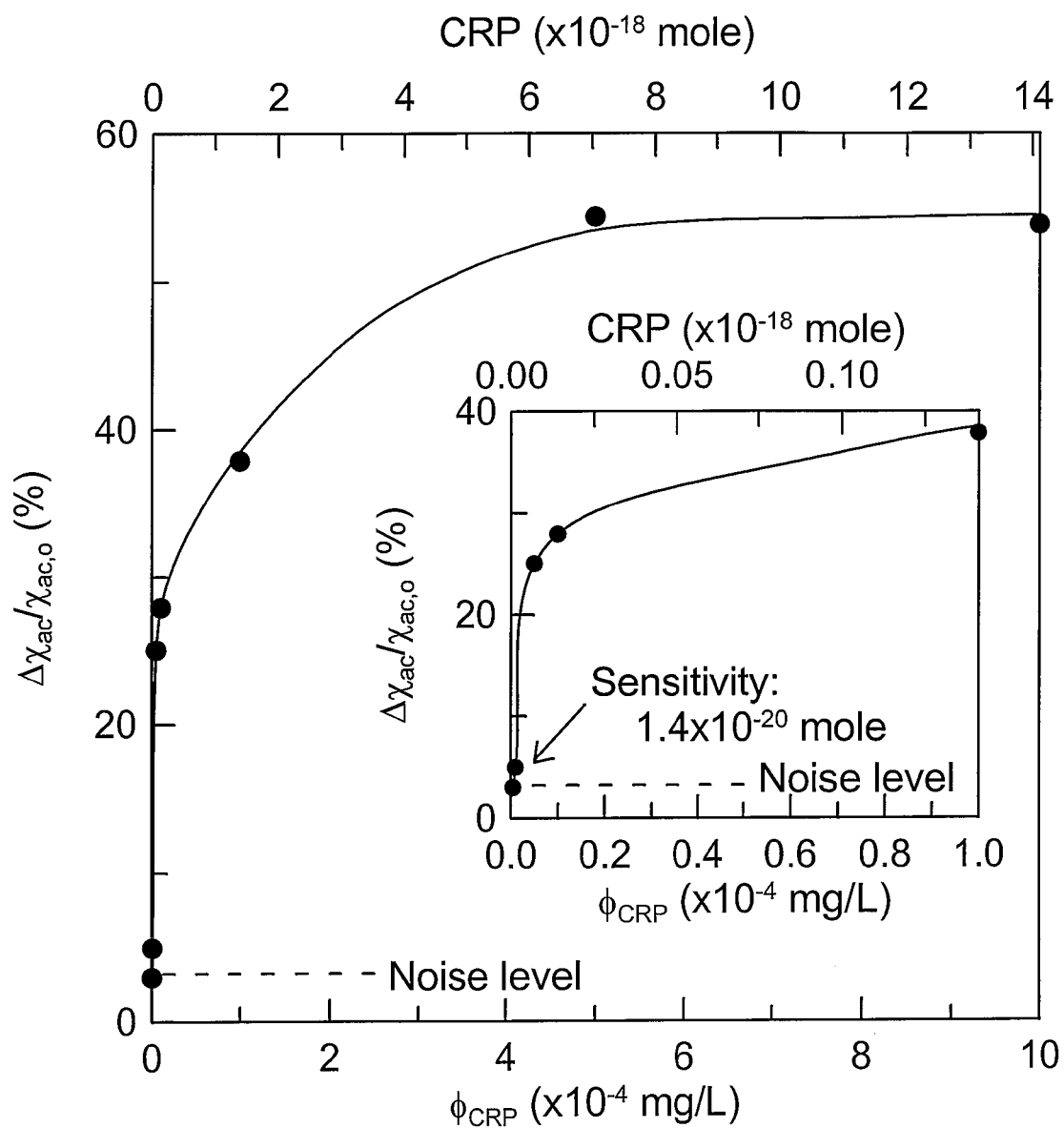
FIG. 6 is a diagram showing $\Delta\chi_{ac,\phi}/\chi_{ac,o}$ as a function of $\phi_{CRP}$ from $5 \times 10^{-7}$ to $10^{-3}$ mg/L, and the $\Delta\chi_{ac,\phi}/\chi_{ac,o}$-$\phi_{CRP}$ curve at lower $\phi_{CRP}$'s is enlarged in the inset.
Figure 7:
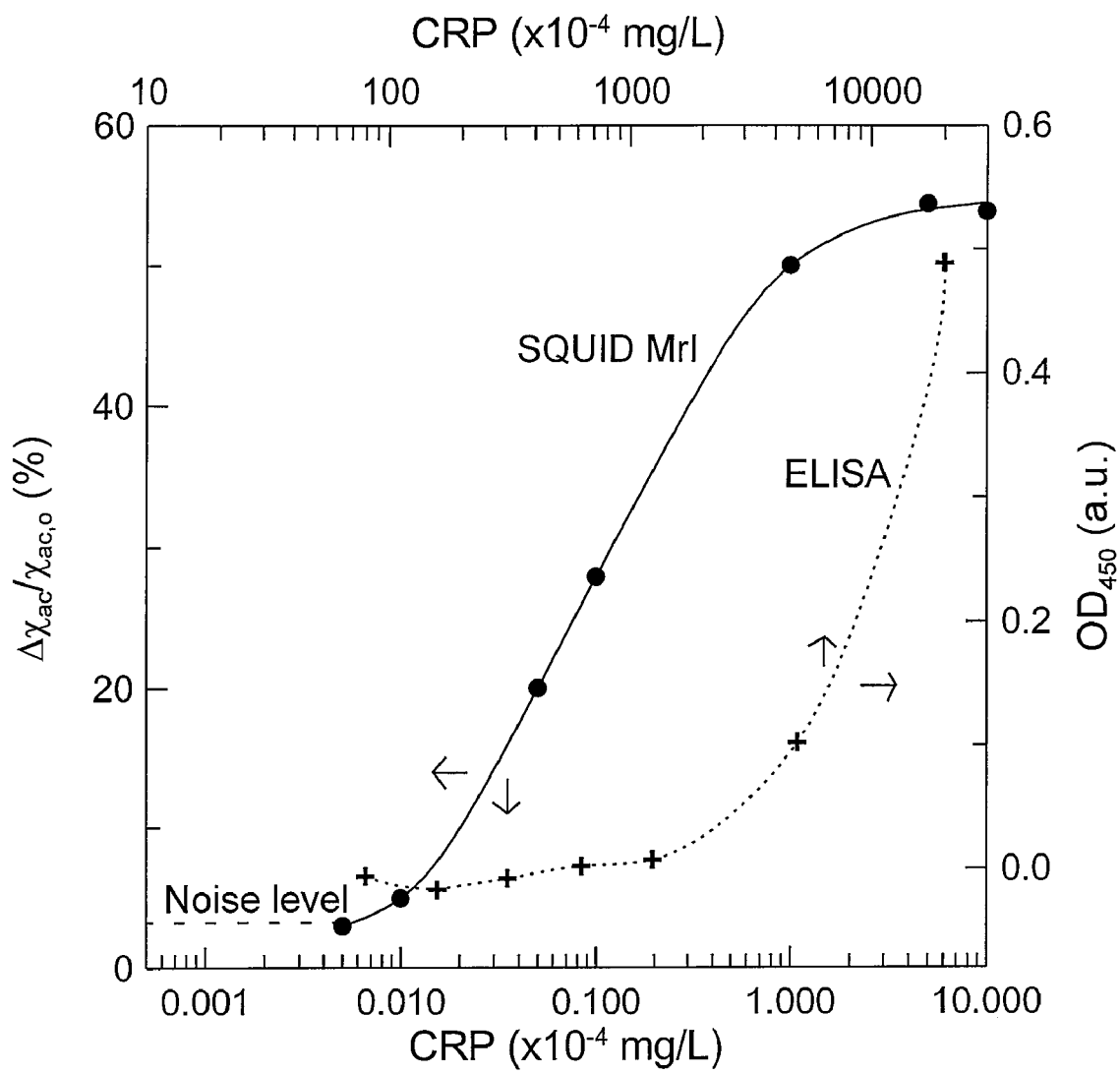
FIG. 7 is a diagram showing the CRP concentration $\phi_{CRP}$ dependent $\Delta\chi_{ac}/\chi_{ac}$ (solid line) and $OD_{450}$ (dashed line).

The $\Delta\chi_{ac,\phi}/\chi_{ac,o}$ as a function of $\phi_{CRP}$ from $5 \times 10^{-7}$ to $10^{-3}$ mg/L is plotted in FIG. 6. The $\Delta\chi_{ac,\phi}/\chi_{ac,o}$ vs. $\phi_{CRP}$ curve at the lower $\phi_{CRP}$'s is enlarged in the insert of FIG. 6. The results clearly demonstrate that the sensitivity in concentration of assaying CRP using the SQUID-based MRA system of the invention is around $10^{-6}$ mg/L, i.e. 1 ppt. Since the volume of the CRP solution is 20 µl, and the molecular weight of CRP is 116.67 KDa, the sensitivity for assaying CRP in mole units is around $1.4 \times 10^{-20}$ mole. To better illustrate the ultra-high sensitivity of the SQUID-based MRA system of the present invention, the $\Delta\Phi_{ac,\phi}/\chi_{ac,o}$ vs. $\phi_{CRP}$ curve is compared with the assaying characteristic curve ($OD_{450}$-$\phi_{CRP}$ curve) via ELISA as shown in FIG. 7 respectively with the solid line and the dash line. It is clear that the sensitivity on assaying CRP via ELISA is around 0.1 mg/L, which is much less sensitive than that of the SQUID-based MRA system by a factor of $10^5$.

Figure 8:
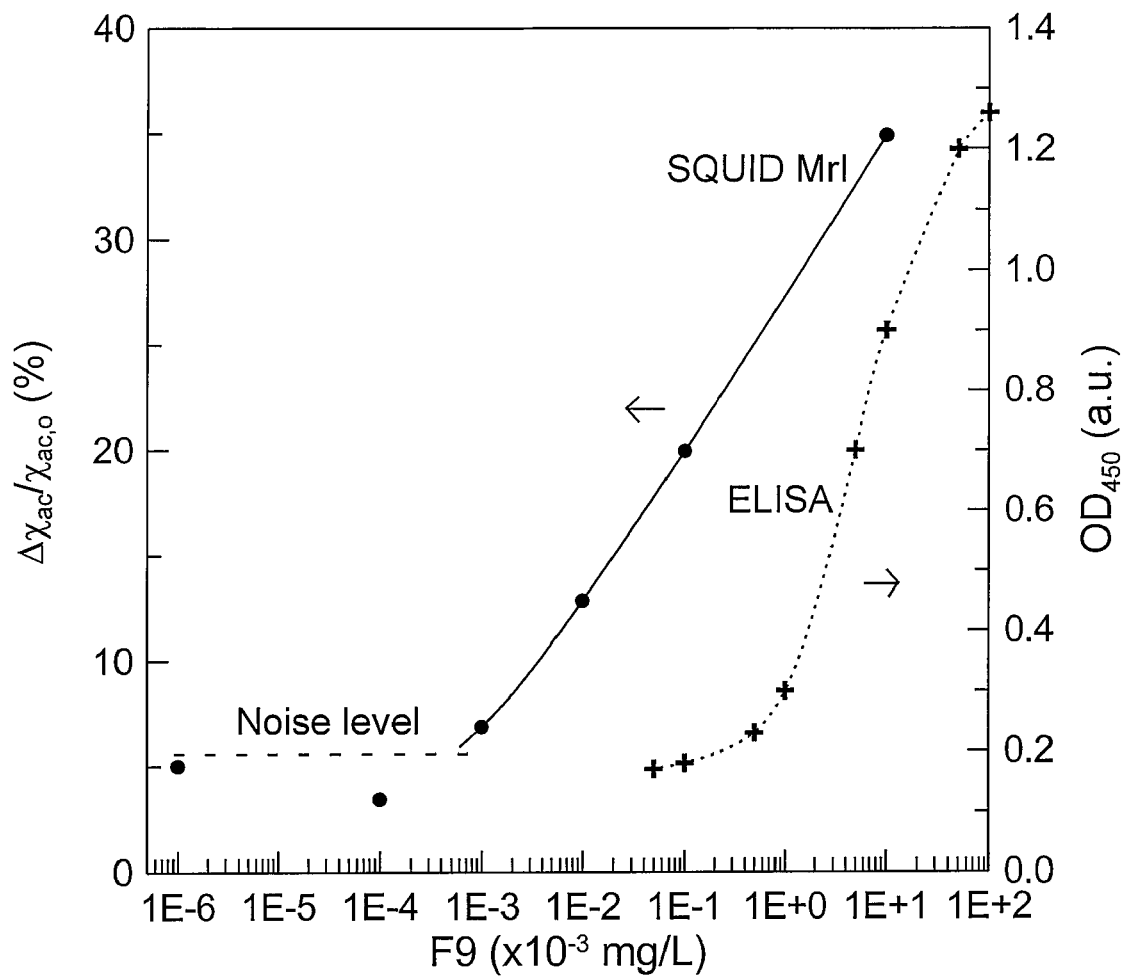
FIG. 8 is a diagram showing the F9 concentration $\phi_{F9}$ dependent $\Delta\chi_{ac}/\chi_{ac}$ (solid line) and $OD_{450}$ (dashed line).

The assaying results on human coagulation factor IX (F9) measured by the SQUID-based MRA system with ultra high sensitivity vs. the conventional ELISA are summarized as follows. F9 circulates in the blood as an inactive zymogen. F9 is converted to an active form by factor XIa, which excises the activation peptide and thus generates a heavy chain and a light chain held together by one or more disulfide bonds. The role of activated F9 in the blood coagulation cascade is to activate factor X to its active form through interactions with $Ca^{+2}$ ions, membrane phospholipids, and factor VIII. Alterations of F9, including point mutations, insertions and deletions induce F9 deficiency, which is a recessive X-linked disorder, and is known as hemophilia B or Christmas disease. It is worthy to note that the anti-mouse-F9 coated on the magnetic nanoparticles in this aspect of the invention is monoclonal. This implies that the F9 in this case is effectively a single-active-epitope molecule. The $\Delta\Phi_{ac,\phi}/\chi_{ac,o}$ curve for F9 via the SQUID-based MRA measurement is plotted with the solid line in FIG. 8. The sensitivity of the SQUID-based MRA system is demonstrated to be $10^{-6}$ mg/L, for example, 1 ppt. For comparison purposes, the $OD_{450}$-$\phi_{F9}$ curve via ELISA is illustrated with the dashed line in FIG. 8. ELISA results demonstrate a sensitivity of $10^{-3}$ mg/L, for example 1 ppb. Accordingly, the sensitivity of ELISA for F9 is just one part of thousand of that of the SQUID-based MRI system. In brief, ultra-high sensitivity is also achievable with the SQUID-based MRA for assaying single-active-epitope molecules.

The assaying results on small-molecule LMG determined by the SQUID-based MRA system with ultra high sensitivity vs. the conventional competitive ELISA are summarized as follows. LMG, having a molecular weight of 23.6 Da, is generally accepted as a small molecule. LMG is the principle metabolite of malachite green in aquatic beings. Malachite green is used medicinally in dilute solution as a local antiseptic or to treat parasites, fungal infections for aquatic eggs and young fry. However, an over dose of LMG may lead to liver cancer for human. Thus, LMG is one kind of carcinogens to human.

Figure 9:
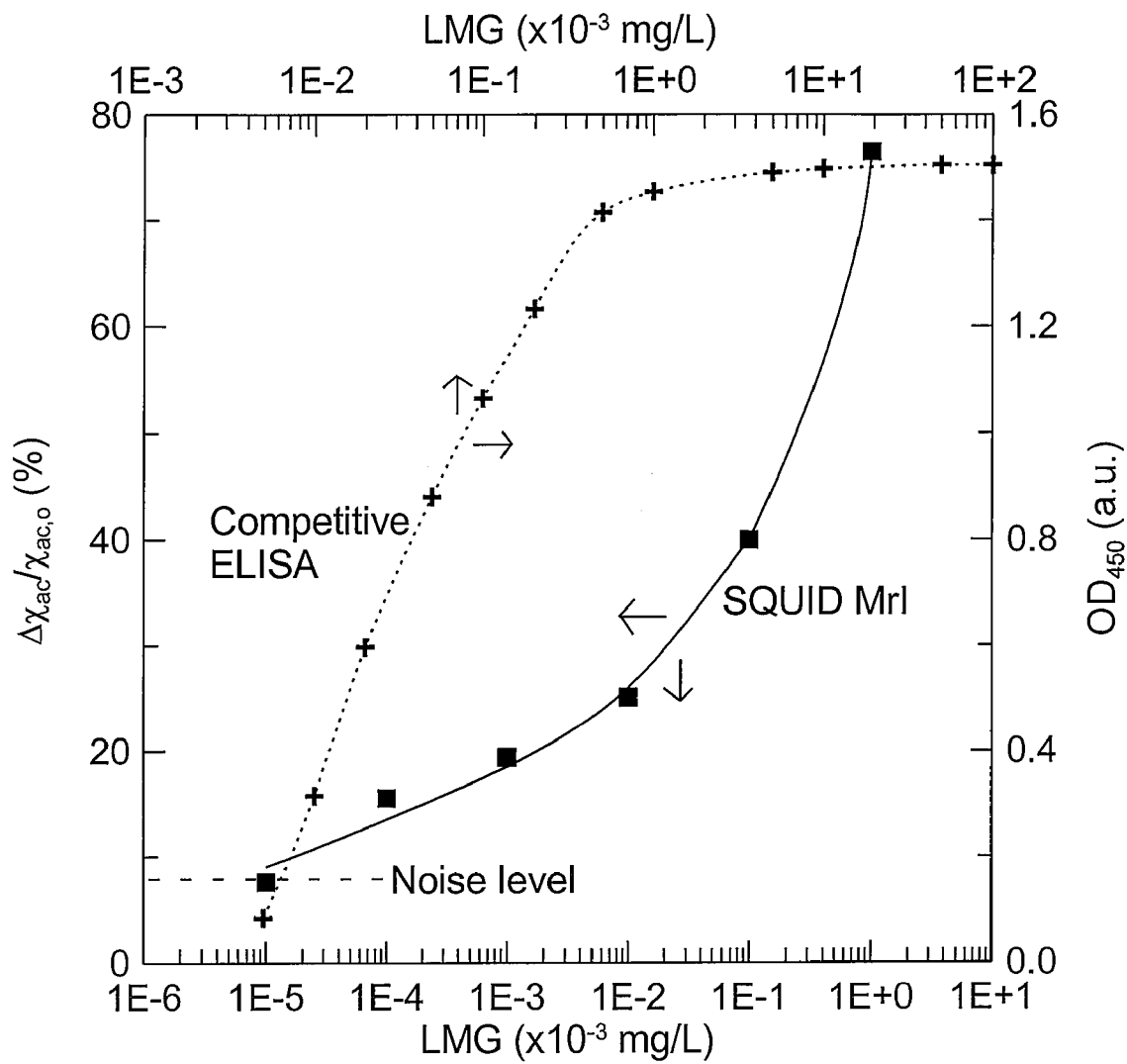
FIG. 9 is a diagram showing the LMG concentration $\phi_{LMG}$ dependent $\Delta\chi_{ac}/\chi_{ac}$ (solid line) and $OD_{450}$ (dashed line).

Referring to FIG. 9, the solid line denotes the characteristic curve for the relationship between the $\Delta\chi_{ac,\phi}/\chi_{ac,o}$ and the LMG concentration $\phi_{LMG}$ via the SQUID-based MRA measurements. The sensitivity is shown to be around $10^{-9}$ mg/L, for example about $10^{-3}$ ppt. The characteristic curve for the relationship between $OD_{450}$ and the LMG concentration $\phi_{LMG}$ is presented with the dashed line in FIG. 9. The sensitivity for competitive ELISA is shown to have a sensitivity of $5\times10^{-5}$ mg/L, for example 0.05 ppb. The results shown in FIG. 9 reveal the fact that the SQUID-based MRA is much more sensitive than ELISA by about four orders of magnitude for assaying small molecules, such as LMG.

In accordance to the present invention, a high-$T_c$ SQUID-based MRA system has been developed for assaying bio-targets including small biomolecules with ultra-high sensitivity. By utilizing the flux-transfer technology, the SQUID sensor is prevented from being disturbed by the ac excited magnetic fields; hence, the SQUID sensor can be stable in a long-time operation. Additionally, the sensor-end loop of the transfer coil can be placed very close to the SQUID, implying that an ultra-high sensitivity achieved for probing detected magnetic signals. The present invention has also demonstrated that the ultra-high sensitive SQUID-based MRA system is applicable to performing assays on multiple-active-epitope molecules, single-active-epitope molecules or small molecules. The assay results show that sensitivity for the SQUID-based MRA system of the invention is 1 ppt or lower. It is believed that the sensitivity could be further improved when antibodies having higher titer to the detected molecules are coated onto magnetic nanoparticles. Accordingly, the SQUID-based MRA is a promising diagnostic tool for detecting proteins, toxic molecules, bacteria, viruses or even DNA at ultra-low levels of concentration.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. An ultra-sensitive method for quantitatively determining a concentration of biomolecules in a sample solution, the method comprising:
   providing a reagent comprising magnetic nanoparticle, wherein the surfaces of the magnetic nanoparticles are coated with bio-receptors;
   measuring an ac magnetic susceptibility of the reagent ($\chi_{ac,o}$) at a mixture frequency ($mf_1+nf_2$), wherein m or n is independently an integer larger than zero;
   mixing the reagent with the sample solution containing the biomolecules that comprise multiple-active-epitope biomolecules or single-active-epitope biomolecules, wherein the bio-receptors coated on the surfaces of the magnetic nanoparticles become associated with the biomolecules;
   measuring the ac magnetic susceptibility of the reagent after the association ($\chi_{ac,\phi}$) with the biomolecules at the mixture frequency ($mf_1+nf_2$);
   calculating a difference in the ac magnetic susceptibility of the reagent ($\Delta\chi_{ac,\phi}$) at the mixture frequency ($mf_1+nf_2$) before and after the association with the biomolecules, wherein $\Delta\chi_{ac,\phi}=(\chi_{ac,o}-\chi_{ac,\phi})$; and
   determining the concentration of the biomolecules in the sample solution.

2. The method according to claim 1, wherein the reagent is formed by suspending the magnetic nanoparticles in a buffer solution, and the magnetic nanoparticles are coated with a hydrophilic surfactant and the bio-receptors are bound to the hydrophilic surfactant.

3. The method according to claim 2, wherein the biomolecules are conjugated with the bio-receptors.

4. The method according to claim 2, wherein the single-active-epitope biomolecules also comprise small biomolecules, in which when the small biomolecules are conjugated with the bio-receptors, each of the small biomolecules is substantially enveloped by only one of the bio-receptors.

5. The method according to claim 2, where the magnetic nanoparticle is selected from the group consisting of $Fe_2O_3$, $Fe_3O_4$, $MnFe_2O_4$, $NiFe_2O_4$, and $CoFe_2O_4$.

6. The method according to claim 2, wherein the hydrophilic surfactant is selected from the group consisting of dextran, protein G, protein A, liposome, and organic acids.

7. The method according to claim 1, wherein the bio-receptors comprise antibodies or antigens.

8. The method according to claim 1 further comprising:
   establishing a characteristic curve between the difference ($\Delta\chi_{ac,\phi}$) in the ac magnetic susceptibility of the reagent and various known concentrations of the biomolecules in a controlled sample; and
   determining the concentration of the biomolecules in the sample solution according to the characteristic curve.

9. The method according to claim 1, wherein a parameter $\Delta\chi_{ac,\phi}/\chi_{ac,o}$ is used as an indicator for the concentration of the biomolecules, where the parameter $\Delta\chi_{ac,\phi}/\chi_{ac,o}$ is defined as $\Delta\chi_{ac,\phi}/\chi_{ac,o}\equiv(\chi_{ac,o}-\chi_{ac,\phi})/\chi_{ac,o}$.

10. The method according to claim 9 further comprising:
    establishing a normalized characteristic curve between $\Delta\chi_{ac,\phi}/\chi_{ac,o}$ and various known concentrations of the biomolecules in a control solution; and
    determining the concentration of the biomolecules in the sample solution according to the normalized characteristic curve.

11. The method according to claim 1, wherein the ac magnetic susceptibility of the magnetic reagent after the association ($\chi_{ac,\phi}$) with the biomolecules is measured without having to remove the free, un-associated biomolecules.

12. The method according to claim 1, wherein the ac magnetic susceptibility of the reagent is measured by a magnetoreduction measurement system comprising:
    a magnetic-flux sourcing unit, for housing the reagent with or without the sample solution, supplying a varying magnetic flux to the reagent and detecting an induced magnetic flux from the reagent;
    a magnetic-flux reading unit, positioned as a location from the magnetic-flux sourcing unit, wherein the magnetic-flux reading unit comprises at least a SQUID to sense the induced magnetic flux; and
    a magnetic-field transfer unit, for transferring the induced magnetic flux of the reagent to the SQUID at the location.

* * * * *